US009170252B2

(12) United States Patent
Harper

(10) Patent No.: US 9,170,252 B2
(45) Date of Patent: Oct. 27, 2015

(54) ASSAY FOR ASSESSMENT OF ENDOSOMAL TRANSPORT

(71) Applicant: SYNTAXIN LIMITED, Abingdon, Oxfordshire (GB)

(72) Inventor: Elaine Harper, Abingdon (GB)

(73) Assignee: IPSEN BIOINNOVATION LIMITED, Abington, Oxfordshire (GB)

( * ) Notice: Subject to any disclaimer, the term of this patent is extended or adjusted under 35 U.S.C. 154(b) by 0 days.

(21) Appl. No.: 14/429,668

(22) PCT Filed: Oct. 23, 2013

(86) PCT No.: PCT/GB2013/052765
§ 371 (c)(1),
(2) Date: Mar. 19, 2015

(87) PCT Pub. No.: WO2014/064442
PCT Pub. Date: May 1, 2014

(65) Prior Publication Data
US 2015/0241408 A1 Aug. 27, 2015

(30) Foreign Application Priority Data

Oct. 23, 2012 (GB) .................................. 1219024.5

(51) Int. Cl.
*G01N 33/53* (2006.01)
*G01N 31/00* (2006.01)
*G01N 33/50* (2006.01)

(52) U.S. Cl.
CPC ........ *G01N 33/502* (2013.01); *G01N 2333/952* (2013.01)

(58) Field of Classification Search
CPC ... A61K 38/00; A61K 38/4893; C07K 14/33; C07K 2319/00; C12N 9/52; G01N 33/6896
See application file for complete search history.

(56) References Cited

FOREIGN PATENT DOCUMENTS

| EP | 2462938 A1 | 6/2012 |
|---|---|---|
| WO | 94/21300 A2 | 9/1994 |
| WO | 95/33850 A1 | 12/1995 |
| WO | 96/33273 A1 | 10/1996 |
| WO | 98/07864 A1 | 2/1998 |
| WO | 99/32272 A1 | 7/1999 |
| WO | 2005/014798 A2 | 2/2005 |
| WO | 2011/018665 A1 | 2/2011 |
| WO | 2011/022357 A3 | 2/2011 |

OTHER PUBLICATIONS

R. Bartz, et al., "Effective siRNA delivery and target mRNA degradation using an amphipathic peptide to facilitate pH-dependent endosomal escape," Biochemical Journal, Jan. 25, 2011, vol. 435: 475-487, Biochemical Society.

A. Fischer, et al., "Bimodal modulation of the botulinum neurotoxin protein-conducting channel," PNAS, Feb. 3, 2009, vol. 106(5): 1330-1335, The National Academy of Sciences of the USA.

S. Ohkuma, et al., "Prodigiosins Uncouple lysosomal vacuolar-type ATPase through promotioin of H+/Cl-symport," Biochemical Journal, Jul. 17, 1998, vol. 334: 731-741.

D. M. Tscherne, et al., "Time- and Temperature-Dependent Activation of Hepatitis C Virus for Low-pH-Triggered Entry," Journal of Virology, Feb. 2006, vol. 80(4): 1734-1741, American Society for Microbiology.

H. Akita et al., "Reprint of: Nanoparticles for ex vivo siRNA delivery to dendritic cells for cancer vaccines: Programmed endosomal escape and dissociation", Journal of Controlled Release, Jan. 5, 2011, pp. 58-64, vol. 149 (1), Elsevier, Amsterdam, NL.

P. J. Zhu et al., "Quantitative high-throughput screening identifies inhibitors of anthrax-induced cell death", Bioorganic & Medical Chemistry, Jul. 15, 2009, pp. 5139-5145, vol. 17(14), Elsevier, Pergamon, GB.

D. K. Bonner et al., "Intracellular Trafficking of Polymidoamine-Poly(ethylene glycol) Block Copolymers in DNA Delivery", Bioconjugate Chemistry, Aug. 8 2011, pp. 1519-1525, vol. 22(8), American Chemical Society.

M. J. Kirchmeier et al., "Correlations between the rate of intracellular release of endocytosed liposomal doxorubicin and cytotoxicity as determined by a new assay", Journal of Liposome Research, Feb. 1, 2001, pp. 15-29, vol. 11 (1), Taylor & Francis, Philadelphia, PA, US.

A. Tamura et al., "Efficient siRNA delivery based on PEGylated and partially quaternized polyamine nanogels: Enhanced gene silencing activity by the cooperative effects of tertiary and quaternary amino groups in the core", Journal of Controlled Release, Sep. 15, 2010, pp. 378-387, vol. 146(3), Elsevier, Amsterdam, NL.

L. J. Bruce et al., "The monovalent cation leak in overhydrated stomatocytic red blood cells results from amino acid substitutions in the Rh-associated glycoprotein", Blood Journal, Feb. 5, 2009, pp. 1350-1357, vol. 113(6), The American Society of Hematology.

S. E. Coles et al., "A variant of hereditary stomatocytosis with marked pseudohyperkalaemia", British Journal of Haematology, Feb. 1999, pp. 275-283, vol. 104(2).

S.Sun et al., "Botulinum Neurotoxins B and E Translocate at Different Rates and Exhibit Divergent Responses to GT1b and Low pH", Biochemistry, Jul. 17, 2012, pp. 5655-5662, vol. 51(28), American Chemical Society Publications.

H. Wartlick, et al., "Highly Specific HER2-mediated Cellular Uptake of Antibody-modified Nanoparticles in Tumour Cells," Journal of Drug Targeting, Informa Healthcare, Aug. 2004, 12(7): 461-471, Taylor & Francis Ltd.

(Continued)

*Primary Examiner* — Lisa Cook
(74) *Attorney, Agent, or Firm* — Morris, Manning & Martin, LLP; Christopher W. Raimund

(57) ABSTRACT

The invention provides an assay and corresponding kit for assessing the delivery efficiency of a molecule into a eukaryotic cell (basic assay). The present invention also provides an assay and corresponding kit for assessing the inhibitory effect of a test molecule in relation to the before-mentioned basic assay.

14 Claims, 8 Drawing Sheets

(56) References Cited

OTHER PUBLICATIONS

Figure 2:
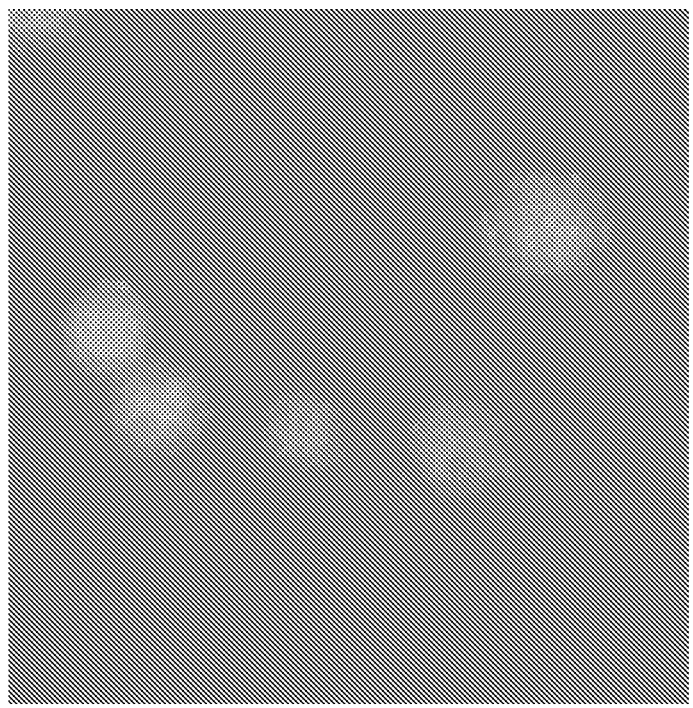
Figure 2:
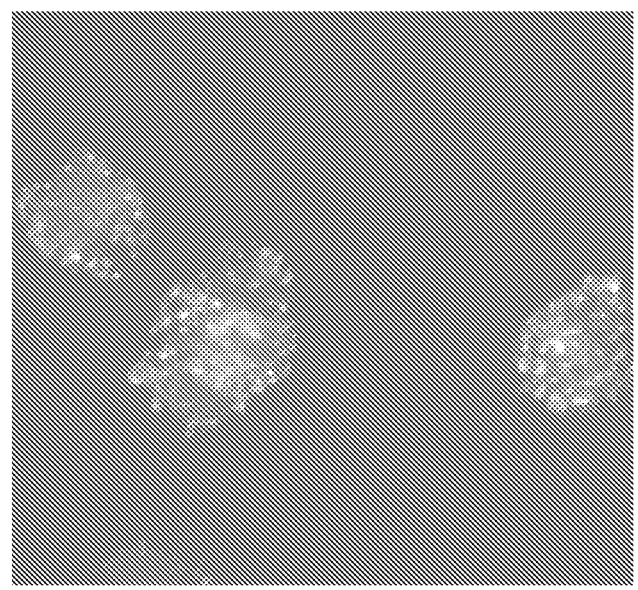

D. Sesardic, et al., "Refinement and Validation of an Alternative Bioassay for Potency Testing of Therapeutic Botulinum Type A Toxin.," Pharmacology & Toxicology, 1996, 78: 283-288, Denmark.

D. Sesardic, et al., "Role of standards in assays of botulinum toxins: international collaborative study of three preparations of botulinum type A toxin.," Biologicals, 2003, 31: 265-276, Elsevier Ltd.

D. M. Tscherne, et al., "Time- and Temperature-Dependent Activation of Hepatitis C Virus for Low-pH-Triggered Entry," Journal of Virology, Feb. 2006, 80(4): 1734-1741, American Society for Microbiology.

Figure 1

A

B

A

B

A

B

ASSAY FOR ASSESSMENT OF ENDOSOMAL TRANSPORT

The present invention relates to an assay and corresponding kit for assessing the delivery efficiency of a molecule into a eukaryotic cell.

A key requirement for efficacy of any potential therapeutic molecule is that it must be able to demonstrate good potency. The present invention relates to molecules that gain entry into the cytosol of eukaryotic cells via the well-known process of endocytosis. With this in mind, it is important to understand the steps involved with the mode of cell entry. Thus, to help illustrate the key steps associated with this mode of cell entry, reference is made to FIG. 1. In step 1, the molecule binds to a binding site (e.g. a receptor or acceptor) present on the cell surface. In step 2, the receptor (plus bound molecule) becomes internalised into the cell—this step is generally referred to as 'endocytosis' or 'endosome formation'. In step 3, following internalisation, the molecule inserts into the endosomal membrane, and effects release of the molecule (or a part thereof) from within the endosome, across the endosomal membrane and into the cytosol of the eukaryotic cell. Once in the cytosol (step 4), the molecule is able to act on its intracellular target (e.g. inhibition of a target molecule, such as proteolytic cleavage of a cellular target protein).

Good potency testing therefore relies on accurate assessment of one or more of the above-identified steps.

To-date, potency testing of molecules capable of entering a eukaryotic cell via 'receptor-mediated endocytosis' has focussed on toxin molecules such as clostridial neurotoxins. By way of example, the following assays have been employed for commercially available clostridial neurotoxins (e.g. botulinum neurotoxin, which is marketed under names such as Dysport™, Neurobloc™, and Botox™).

The mouse $LD_{50}$ assay is currently the only assay approved by the FDA for release of botulinum toxins. The assay simultaneously tests the action of all three domains of a botulinum neurotoxin (i.e. binding, translocation, and protease). In more detail, it defines the median lethal intraperitoneal dose of the toxin at a defined time-point usually 2-4 days after dosing (activity is expressed in mouse $LD_{50}$ units). Regrettably, however, $LD_{50}$ assays use large numbers of animals. Moreover, $LD_{50}$ units are not absolute measurements because they are not biological constants—as such they are highly dependent on the assay conditions. In particular, errors associated with this assay can be as high as 60% between different testing facilities (Sesardic et al. 2003; Biologicals 31 (4):265-276).

The mouse flaccid paralysis assay, which is also known as the 'mouse abdominal ptosis assay', relates the activity of botulinum toxin to the degree of abdominal bulging seen after the toxin is subcutaneously injected into the left inguinocrural region of a mouse—the magnitude of the paralysis is dose-dependent. This approach has been proposed as a refinement to the mouse $LD_{50}$ test, because it relies on a humane endpoint. This assay is approximately 10 times more sensitive than the $LD_{50}$ assay, uses a sub-lethal dose of toxin and is more rapid than the $LD_{50}$ test as it provides results in 24 to 48 hours, compared to 72 to 96 hours for a typical $LD_{50}$ assay. The results from this assay show excellent agreement with the $LD_{50}$ values (Sesardic et al., 1996). Although this assay uses 20% of the animals used in the $LD_{50}$ assay it still necessitates the use of animals.

Assays such as the mouse/rat phrenic nerve hemi-diaphragm assay (which are based on the use of ex vivo nerve muscle preparations) relate the activity of botulinum neurotoxin to a decrease in the amplitude of a twitch response of the preparation after it is applied to a maintenance medium. The usual endpoint of the assay is the time required before a 50% decrease in amplitude is observed. Regrettably, however, the hemi-diaphragm assay (like the $LD_{50}$ assay) results in the use of large numbers of animals. In addition, the assay requires highly skilled personnel trained in the use of sophisticated and expensive equipment.

Substrate cleavage assays using cultured spinal cord neurons relate the activity of botulinum neurotoxin to the cleavage of a specific protein present in said neurons. Whilst the assay uses fewer animals than the in vivo ($LD_{50}$, mouse flaccid paralysis assay) and ex vivo assays (hemi-diaphragm), the assay requires highly skilled personnel to perform the dissection and cultures—the dissection and culture techniques are time-consuming and must be planned ~3 weeks in advance of when they are required. A further drawback is that substrate cleavage measurements can be highly variable.

All of the above assays have particular failings, notably animal welfare issues and/or limitation to the testing of molecules that bind to the neuromuscular junction (NMJ)—the latter being the target cells to which a natural clostridial neurotoxin binds.

WO95/33850 describes a cell-free substrate cleavage assay in which the cleaved product is detected by an epitope-specific antibody. Since the antibody is able to distinguish cleaved substrate from uncleaved substrate protein, it is possible to quantify the potency of a clostridial neurotoxin. Whilst this assay does not suffer from the above-identified animal welfare or NMJ specific shortfalls, it is indeed a 'cell-free' assay and, as such, is only capable of assessing potency in the sole context of protein cleavage. Accordingly, WO95/33850 is not able to assess potency in the context of any one or more of the equally important steps, notably: cell binding; endosome formation; or translocation across the endosomal membrane. Put another way, a molecule identified (according to WO95/33850) as an efficient substrate-cleaving molecule may have little or no useful therapeutic potency—for example, because it lacks any one or more of: optimal cell binding; optimal endosome formation; and/or optimal translocation function.

There is therefore a need in the art for an alternative and/or improved potency assay, which addresses one or more of the above-identified problems. For example, there is a need for a humane assay that addresses existing animal welfare problems. Similarly, there is a need for an assay that is not limited to the testing of molecules that specifically bind to the NMJ and/or to neuronal cells. Similarly, there is a need for an assay that provides reliable potency results for molecules, in particular for an assay that provides potency results reflective of in vivo potency.

The present invention addresses the above-identified problems by providing an assay that comprises:

i) contacting a eukaryotic cell with a test molecule that is to be assessed for endosome release ability, wherein said eukaryotic cell comprises a cell membrane including a Binding Site present on the outer surface of the cell membrane of said cell;

ii) incubating the test molecule with said eukaryotic cell, and thereby allowing a) the test molecule to bind to and form a bound complex with the Binding Site present on the eukaryotic cell, thereby permitting said bound complex to enter the eukaryotic cell by endocytosis;

b) one or more endosomes to form within said cell, wherein the one or more endosomes contain the test molecule; and c) said test molecule to enter the cytosol of the eukaryotic cell by crossing the endosomal membrane of the one or more endosomes;

iii) removing excess test molecule that is not bound to the Binding Sites present on the eukaryotic cells;

iv) after a predetermined period of time, detecting the amount of test molecule present in the one or more endosomes, or detecting the amount of test molecule present in the cytosol of said eukaryotic cell;

v) comparing the amount of test molecule detected in step iv) with a control value, wherein said control value represents the amount of test molecule present in the one or more endosomes or the amount of test molecule present in the cytosol prior to step iv);

vi) calculating an endosome release value for the test molecule by determining the relative change in the amount of test molecule that is present within the one or more endosomes, or by determining the relative change in the amount of test molecule present in the cytosol of said eukaryotic cell.

The eukaryotic cell may be selected from a yeast cell, an insect cell, a vertebrate cell, a mammalian cell, a plant cell, and a fungal cell. Examples of such animal cells include human, rodent, mouse, and hamster cells.

In one embodiment the eukaryotic cell Binding Site is capable of either receptor-mediated endocytosis or non-receptor mediated endocytosis. The Binding Site may be a receptor or an acceptor. Examples of peptide sequences that are endocytosed via non-receptor Binding Sites include peptides having arginine-rich sequences (e.g. RRRRRRRR, RRRRRRRW), and peptides such as PHLIP, Pep-1, SAPE, PFVYLI, and Kaposi FGF derived AAVALIPAVILALLAP. These peptides are believed to be endocytosed into cells via non-specific ionic interactions. The Binding Site may be a Binding Site that occurs naturally on the cell surface of a eukaryotic cell. Alternatively, a eukaryotic cell may be a recombinant eukaryotic cell that has been modified to express a Binding Site that would not occur naturally on the cell surface of said eukaryotic cell.

Incubation step ii) may proceed for any given time period, for example for a time period from 5 minutes to 5 days. A typical time period is 1-12 hours, for example 2-10 hours, 4-8 hours, or 6-8 hours. During this period, the eukaryotic cell (i.e. the outer surface of the cell membrane) is exposed to test molecule (typically an excess of test molecule) with the result that a 'steady state' is achieved in which test molecule enters and leaves the intracellular endosomes at approximately the same rate. This point in time represents an optimal time point at which to perform steps iii and/or iv).

Step iii) involves reducing or removing the source of test molecule external to the eukaryotic cell, thereby reducing the amount of (or substantially preventing) test molecule entering the cell. Said reduction in the amount of test molecule entering the eukaryotic cell, in turn, provides a change in the amount of test molecule entering the endosomes, which in turn results in a change in the amount (or rate) of test molecule leaving the endosomes and/or entering the cytosol of the eukaryotic cell. It is the amount (or rate) of test molecule leaving the endosome structures that provides the basis of the assay of the present invention—said amount (or rate) of test molecule leaving the endosome structures may be measured by a change in the amount of test molecule present in the endosomes and/or by a change in the amount of test molecule present in the cytosol. When measuring the amount of test molecule present in the endosomes, a reduction in the amount of test molecule present is typically observed. When measuring the amount of test molecule present in the cytosol, an increase or decrease in the amount of test molecule present within the cytosol may be observed. By way of example, an increase in the amount of test molecule in the cytosol may be observed when step iii) is initiated prior to establishment of steady state endosomal transport of the test molecule. Alternatively, a decrease in the amount of test molecule in the cytosol may be observed when the rate of cellular secretion of the test molecule from the eukaryotic cell exceeds the rate of endosomal transport of the test molecule from the endosomes into the cytosol.

The eukaryotic cells employed in the assay may be immobilised on a surface. Immobilisation of the cells may be performed as a pre-assay step (i.e. pre-immobilization), or may be performed as part of the assay protocol. Thus, in one embodiment, the cells of the assay are pre-immobilized. Immobilisation of the eukaryotic cells may be performed by any conventional means. By way of example, cells are seeded into the assay plates at high density and allowed to adhere before the assay is conducted. Alternatively, cells are seeded into assay plates and cultured for several days before use to provide a confluent monolayer. Cell attachment may be enhanced by using conventional coatings, such as poly-D-lysine coated plates.

In one embodiment, immobilisation of the eukaryotic cells may be performed prior to or during step iii), thereby providing a simple means for separating said cells from free (e.g. unbound or exogenous) test molecule. Alternatively, immobilisation may be performed after step iii), for example to facilitate detection step iv).

Step iii) may include a filtering step or affinity ligand step during which the eukaryotic cells are separated from excess (e.g. unbound or exogenous) test molecule. Step iii) may include a washing step in which excess (e.g. unbound or exogenous) test molecule is washed away from the eukaryotic cells, for example using a conventional buffer. Excess test molecule is intended to mean test molecule that is present in the assay medium, external to the eukaryotic cells, and which has not yet become bound to a Binding Site present on the surface of the eukaryotic cells.

Detection of test molecule in step iv) is typically performed shortly after step iii). By way of example, a typical timeframe for step iv) is between 5 minutes and 5 hours following step iii). In one embodiment, step iv) is performed 15-240 minutes, or 30-180 minutes, or 45-150 minutes following step iii). Detection step iv) may be repeated over several time points, for example at intervals of 10 minutes or 15 minutes or 30 minutes—this will permit a rate of endosomal release to be calculated.

Detection step iv) may be performed by any conventional means. By way of example, detection independent of permeabilisation can be achieved by monitoring the test molecule itself. This can be achieved by tagging the test molecule with a fluorophore. Suitable fluorophores that can be attached to the test molecule include fluorescein, rhodamine, green fluorescent protein, single walled carbon nanotubes and AlexaFluor® 488.

Detection of the test molecule may be based upon intracellular localisation of said test molecule—an example of such localisation within the cytosol is localisation to the cell nucleus. In this embodiment, the test molecule is labelled (e.g. with a fluorophore) and also posesses a nuclear localisation signal. Thus, label can be detected in the endosome and endosomal escape determined by monitoring accumulation of label (e.g. fluorescence) in the cell nucleus. In this regard, the nucleus itself may be labelled with a dye—conventional nuclear dyes are well known in the art (e.g. Hoescht stain).

Any conventional detection means may be employed for monitoring the test molecule, such as Fluorescence Resonance Energy Transfer (FRET). By way of example, the donor/acceptor pair can be cyan fluorescent protein (CFP) and yellow fluorescent protein (YFP). Other donor/acceptor pairs for use in FRET are well known in the art. In one embodiment, the test molecule labelled with CFP and YFP can be detected, and the amount of the test molecule present in the endosome and/or cytosol can be determined. In one embodiment, the loss of a FRET signal may be monitored. For example, should only part of the test molecule be translocated from the endosome into the cytoplasm, this could lead to loss of the FRET signal if the donor/acceptor pair (e.g. CFP and YFP) becomes separated. Thus, for example, the test molecule may comprise (or consists of) the L-chain and $H_N$ domain of a clostridial neurotoxin (or derivatives or functional equivalents thereof, e.g. a TSI). The donor/acceptor labels (e.g. CFP and YFP) may be placed on said two components, for example the L-chain may be labelled with CFP and the $H_N$ component may be labelled with YFP. In one embodiment, the FRET signal is detectable whilst the test molecule comprising $LH_N$ is present in the cell endosome. The translocation function of the $H_N$ component then releases the therapeutic moiety (i.e. L-chain) into the cytosol, and the FRET signal disappears as the CFP and YFP labels become separated from one another.

Bioluminescence Resonance Energy Transfer (BRET) may also be used to monitor/detect the test molecule. In BRET, the donor fluorophore of the FRET pair is replaced by a luciferase. Suitable BRET methodologies are known to those skilled in the art.

In one embodiment, detection of the test molecule may be based on the natural pH difference that exists within an endosome vis-a-vis the pH of the cytosol. In this embodiment, the test molecule may be labelled with a pH-sensitive label, such as a pH-sensitive dye. The label may selected to be detectable/visible (e.g. with increased intensity) in a specific pH range. Thus, the label may be chosen to only be detectable/visible (e.g. with higher intensity) when present in the endosome, and invisible/undetectable (e.g. with lower intensity) when present in the cytosol. Alternatively, the label may be chosen to only become detectable/visible upon translocation of the test molecule into the cytosol. Suitable labels (e.g. dyes) are known to those skilled in the art such as flourescein-based pH-indicators (e.g. BCECF, BCPCF) and derivatives thereof, benzoxanthene dyes, cyanine-based dyes, and other small molecule pH indicators (e.g. europium complex, fluorene derivatives, 1,4-Dihydroxyphthalonitrile (1,4-DHPN), 8-Hydroxypyrene-1,3,6-trisulfonic acid (HPTS)), acidic pH indicators such as a pyridyl oxazol probe Yellow/Blue DND-160 PDMPO 59, the anthrathene-based sensor DND-167 60, DND-189 61, DND-153 62, and DND 192 63, BODIPY-Based Dyes (e.g. BODIPYs 68, NH2BDP 68a, DiMeNBDP 68b, EtMeNBDP 68c, and DiEtNBDP 68d) and pHrodo Indicators.

Depending on the type of detection means employed, it may be desirable to permeabilise the eukaryotic target cells. By way of example, a protein or non-protein tag (such as a myc tag or biotin) may be attached to the test molecule or the test molecule itself may inherently include a detectable component (such as an epitope), and subsequent detection may be achieved using a labelled primary antibody or an unlabelled primary antibody together with a labelled secondary antibody. Antibody detection reagents and methodologies are well known and routine to those skilled in the art. Similarly, binding partners are well known in the art, and for example labelled streptavidin may be used to detect a biotinylated control molecule. Permeabilisation typically includes an initial fixing step (e.g. with formaldehyde, paraformaldehyde, ethanol or methanol) followed by permeabilisation with an appropriate agent—conventional permeabilisation agents are well known in the art (e.g. triton X-100, digitonin, tween 20 and/or saponin).

Comparison step v) employs the use of a control value, which represents the amount of test molecule present in the endosomes and/or cytosol prior to detecting step iv). The control value is typically determined by the same means/method by which the amount of test molecule is determined in detection step iv). The control value typically represents the amount of test molecule present in the endosomes and/or cytosol during or before step iii). By way of example, the control value may represent the amount of test molecule present in the endosomes and/or cytosol during or at the end of step ii)—in one embodiment, the control value represents the amount of test molecule that is present in the endosomes and/or cytosol when a 'steady state' translocation rate has been established, namely when test molecule enters and leaves the intracellular endosomes at approximately the same rate.

The test molecule may be a 'small molecule' therapeutic such as fingolimod, monastrol, pamidronate, methotrexate, buspirone, nemonaprde, apipipiprazole, bifeprunox, SKF82958, octreotide, MK-5046, F038-WE-05, rilmenidine, SCH655842, salvinorin, CP55940 or a nanoparticle. Nanoparticles have been successfully targeted to and shown to be internalised into cells by targeting through an antibody (see, for example, Wartlick et al., J. Drug Target. 12: 461-471). Thus, in one embodiment, the test molecule may be a nanoparticle linked to, inter alia, a Targeting Moiety component such as an antibody or a ligand to a receptor present on the assay cells.

Alternatively, the test molecule may be a larger molecule such as a polypeptide or protein. Particular examples include toxins, such as cytotoxic proteins and non-cytotoxic proteins. In this regard, reference to polypeptides and proteins includes both naturally-occurring and recombinantly prepared polypeptides and proteins.

Cytotoxic proteins act by killing their natural target cells. This group of toxins is exemplified inter alia by plant toxins such as ricin, and abrin, and by bacterial toxins such as diphtheria toxin, and Pseudomonas exotoxin A. Cytotoxic toxins typically kill their target cells by inhibiting the cellular process of protein synthesis. This class of protein includes retargeted cytotoxic proteins in which the natural binding ability of the protein has been modified by the introduction of a binding ligand (also known as a Targeting Moiety), thereby conferring new target cell binding properties on the modified protein.

In contrast, non-cytotoxic proteins act on target cells by incapacitating cellular function. Importantly, non-cytotoxic toxins do not kill the target cells upon which they act. Some of the best known examples of non-cytotoxic proteases include clostridial neurotoxins (e.g. botulinum neurotoxin, which is marketed under names such as Dysport™, Neurobloc™, and Botox™), IgA proteases (see, for example, WO99/032272), and antarease proteases (see, for example, WO2011/022357). Non-cytotoxic proteases act by proteolytically-cleaving and thus inactivating intracellular transport proteins known as SNARE proteins (e.g. SNAP-25, VAMP, or Syntaxin)—see Gerald K (2002) "Cell and Molecular Biology" (4th edition) John Wiley & Sons, Inc. The acronym SNARE derives from the term Soluble NSF Attachment Receptor, where NSF means N-ethylmaleimide-Sensitive Factor. SNARE proteins are essential components of the vesicular secretion process in eukaryotic cells. Thus, non-cytotoxic proteases act by suppressing cellular secretion. This class of protein includes re-targeted non-cytotoxic proteins in which the natural binding ability of the protein has been modified by the introduction of a binding ligand (also known as a Targeting Moiety), thereby conferring new target cell binding properties on the modified protein. Applicant has pioneered the technology relating to the re-targeting of non-cytotoxic proteases, which dates back to the 1990s (see, for example, WO 94/21300, WO 96/33273 and WO 98/07864). Said re-targeted proteins are referred to (throughout the literature and scientific community) as Targeted Secretion Inhibitors (TSIs)—reference to TSIs includes structural equivalents such as those described in WO 2011/018665.

The "test molecule" assay aspect of the present invention may further include a step of detecting in situ activity of the test molecule. For example, in the context of a clostridial neurotoxin or a TSI, the assay may further comprise a step of detecting SNARE protein cleavage. Any such detection means may be employed such, for example, the method described in WO95/33850 or by FRET assay.

The assay of the present invention may be separately employed to assess the inhibitory effects of a blocking molecule on endosomal transport system of a eukaryotic cell. Thus, in a related aspect, the present invention provides an assay that comprises:
i) contacting a eukaryotic cell with a control molecule that binds to a Binding Site present on the surface of said eukaryotic cell, wherein said control molecule forms a bound complex with the Binding Site, enters the eukaryotic cell by endocytosis during which an endosome is formed that contains the control molecule, and wherein said control molecule enters the cytosol of the eukaryotic cell by crossing the endosomal membrane of the endosome;
ii) incubating the control molecule with said eukaryotic cell, and thereby allowing
   a. the control molecule to bind to and form a bound complex with the Binding Site present on the eukaryotic cell, thereby permitting said bound complex to enter the eukaryotic cell by endocytosis;
   b. one or more endosomes to form within said cell, wherein the one or more endosomes contain the control molecule; and
   c. said control molecule to enter the cytosol of the eukaryotic cell by crossing the endosomal membrane of the one or more endosomes;
iii) contacting the eukaryotic cell with a test inhibitor molecule that is to be assessed for its ability to suppress endosomal release of control molecule from one or more endosomes. Said contact of the eukaryotic cell with the test inhibitor molecule may be performed before, during or after step i) and/or during or after step ii);
iv) after a predetermined period of time, detecting the amount of control molecule present in the one or more endosomes, or detecting the amount of control molecule present in the cytosol of said eukaryotic cell;
v) comparing the amount of control molecule detected in step iv) with a control value, wherein said control value represents the amount of control molecule present in the one or more endosomes or the amount of control molecule present in the cytosol prior to step iii);
vi) assigning an inhibition value for the test inhibitor molecule by determining the relative change in the amount of control molecule that is present within the one or more endosomes, or by determining the relative change in the amount of control molecule present in the cytosol of said eukaryotic cell.

The control molecule may be a 'small molecule' therapeutic as mentioned above such as an inhibitor of PMSA (see Liu et al., 2008) or fingolimod, monastrol, pamidronate, methotrexate, buspirone, nemonaprde, apipipiprazole, bifeprunox, SKF82958, octreotide, MK-5046, F038-WE-05, rilmenidine, SCH655842, salvinorin, CP55940 or a nanoparticle.

Alternatively, the control molecule may be a larger molecule such as a polypeptide or protein. Particular examples include toxins, such as cytotoxic proteins and non-cytotoxic proteins. In this regard, reference to polypeptides and proteins includes both naturally-occurring and recombinantly prepared polypeptides and proteins. Examples of suitable cytotoxic and non-cytotoxic proteins have been described hereinbefore. With regard to non-cytotoxic proteins, preferred examples include clostridial neurotoxins (such as tetanus toxin, BoNT/A, BoNT/B, BoNT/$C_1$, BoNT/D, BoNT/E, BoNT/F, BoNT/G, or *C. butyricum*, including natural and modified versions thereof, as well as combinations thereof), TSIs (such as those as hereinbefore described), antarease proteases, and IgA proteases.

Examples of test inhibitor molecules include pore-blockers such as toosendanin—see Fischer, A. et al. (2009) PNAS, Vol. 106, No. 5, pp. 1330-1335; proton-ATPase blockers such as bafilomycin A—see Bartz et al. (2011) Biochem J 435 pp. 475-487, concanamycin A (Tscherne et al. (2006) J Virol, Vol. 80, No. 4, pp. 1234-1741 and prodigiosins—see Ohkuma et al. (1998) J Biochem Vol. 334, pp. 731-741.

All steps as hereinbefore described with reference to the basic assay of the present invention apply equally to the above-described test inhibitor molecule assay.

Contacting step iii) in the above-described test inhibitor molecule assay may proceed for any given time period, for example for a time period from 5 minutes to 5 days prior to the start of the incubation step ii), such as between 30 minutes and 12 hours or between 30 minutes and 10 hours or between 30 minutes and 8 hours or between 1-8 hours following the start of incubation step ii). Alternatively, step iii) may be performed for the same length of time as step ii) or its start may be deferred from 5 minutes to 5 days, such as 1-12 hours or 2-10 hours or 4-8 hours or 6-8 hours. Typically, contacting step iii) is performed once a 'steady state' is achieved (via step ii)) in which control molecule enters and leaves the intracellular endosomes at approximately the same rate The inhibitor aspect of the present invention may also include a step of removing excess control molecule and/or test inhibitor molecule. Said 'removing step' is designated "step iiia)" in the context of the inhibitor aspect assay. All hereinbefore described embodiments of 'removing' step iii) in the context of the "test molecule" assay aspect of the present invention apply equally to the 'removing' step iiia) of the "inhibitor molecule" assay aspect of the present invention.

LIST OF FIGURES

FIG. 1
Key steps associated with endocytosis. The 4 key steps are marked 1-4.

FIG. 2
Internalisation of a TSI targeted to GH3 cells expressing the GHRHR. FIG. 2A: cells were incubated in the absence of TSI. FIG. 2B: cells were incubated in the presence of 3 μM of a TSI with a GHRH targeting moiety for 60 minutes.

Figure 3:
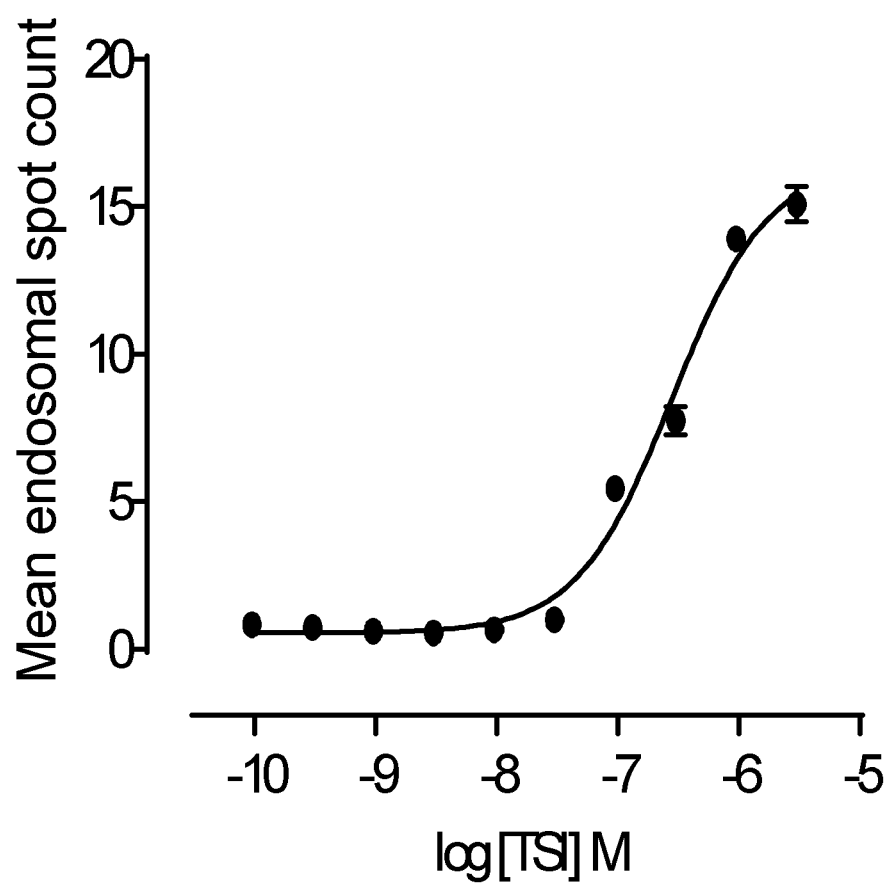

FIG. 3
Concentration-dependent internalisation of a TSI targeted to GH3 cells expressing the GHRHR.

FIG. 4

Internalisation of a TSI targeted to rat pituicytes. FIG. 4A: cells were incubated in the absence of TSI. FIG. 4B: cells were incubated in the presence of 1 μM of a TSI with a GHRH targeting moiety for 60 minutes.

FIG. 5

Concentration-dependent internalisation of a TSI with a GHRH targeting moiety into rat pituicytes. Cells were incubated with: (●) a TSI having a GHRH targeting Moiety; (○) the corresponding unliganded TSI for 60 minutes.

FIG. 6

Internalisation and endosomal escape of a TSI targeted to GH3 cells expressing the rat GHRHR. Continuous treatment regimen is compared to a pulse-chase treatment format.

FIG. 7

Internalisation of a TSI targeted to HT-1080 cells. FIG. 7A: cells were incubated in the absence of TSI. FIG. 7B: cells were incubated in the presence of 2 μM of a TSI with a EGFR targeting moiety for 60 minutes.

FIG. 8

Concentration-dependent internalisation of a TSI targeted to CHO-K1 cells expressing the GHRHR.

EXAMPLES

Example 1

A549 cells are seeded into 96-well plates and cultured for 2 days to achieve ~90% confluence. Alexa-Fluor® 488 labelled epidermal growth factor (EGF) is incubated with cells for 60 minutes. Cells are washed and after increasing incubation times, total cell fluorescence, endosome spot count and endosomal fluorescence determined using high content screening.

Example 2

GH3 cells expressing the rat growth hormone-releasing hormone (GHRH) receptor are seeded into poly-D-lysine coated 96-well plates. After 24 hours, a TSI comprising a targeting domain of GHRH (1-44) and translocation and light chain domains of serotype C botulinum neurotoxin is incubated with cells for 30 minutes. Cells are washed and TSI bound to the cell surface is removed by acid wash at increasing incubation time. Cells are fixed with paraformaldehyde and permeabilised using digitonin. The TSI light chain of botulinum neurotoxin C is detected using a rabbit anti LC botulinum neurotoxin C primary antibody and a goat anti rabbit Alexa-Fluor® 488 labelled secondary antibody. Accumulation into endosomes and endosomal escape is monitored using high content screening.

Example 3

Embryonic spinal cord neurones are prepared and cultured in matrigel-coated 96-well plates. Botulinum neurotoxin A is incubated with neurones for 10 minutes after which the cells are washed. Cells are permeabilised using saponin after increasing incubation time and the LC of botulinum neurotoxin detected using an anti-botulinum neurotoxin LC of A antibody. Accumulation into endosomes and endosomal escape is monitored using high content screening.

Example 4

HEK293 cells expressing the human parathyroid hormone receptor PTH1 are seeded into poly-D-lysine coated 96-well plates. After an overnight incubation cells are incubated with myc-tagged PTH (1-34) for 45 minutes. Cells are washed and after increasing incubation time, cells are fixed and permeabilised with tween 20. Myc-tagged PTH(1-34) is detected using a rhodamine labelled anti-myc antibody. Accumulation into endosomes and endosomal escape is monitored using high content screening.

Example 5

CHO-K1 cells expressing the vasoactive intestinal peptide 1 receptor are seeded into 96-well plates and incubated overnight. Cells are incubated alone or with increasing concentrations of an inhibitor of endosomal escape for 60 minutes after which a biotinylated TSI is co-incubated with the cells for 20 minutes. The TSI is removed by washing and cells fixed at after increasing incubation time using paraformaldehyde. Cells are permeabilised using digitonin and biotinylated. TSI is detected using streptavidin and an Alexa-Fluor® 488 labelled anti-streptavidin antibody. Accumulation of the TSI into endosomes and endosomal escape is monitored by high content screening. The effect of the inhibitor is assessed by a reduced rate of endosomal escape compared to control cells not incubated with inhibitor.

Example 6

GH3 cells expressing the rat GHRH-R were seeded into 96-well plates and incubated overnight. Cells were incubated in the (B) presence and (A) absence of 3 μM of a TSI with a GHRH Targeting Moiety for 60 minutes. Cells were fixed and probed with rabbit antibody to light chain of the TSI and Goat anti-rabbit Alexa Fluor® 488. Nuclei were stained using Hoescht stain. (A) nuclei shown in pale grey with no punctate white spots detected. (B) nuclei shown stained in pale grey (FIG. 2).

Example 7

GH3 cells expressing the rat GHRH-R were seeded into 96-well plates and incubated overnight. Cells were incubated with increasing concentrations of a TSI with a GHRH Targeting Moiety for 60 minutes. Cells were fixed and probed with rabbit antibody to light chain of the TSI and Goat anti-rabbit Alexa Fluor® 488. Endosome spot count was measured by high content screening. Data are the mean±s.e. mean of that obtained in three experiments performed in triplicate (FIG. 3).

Example 8

Figure 4:
Figure 4:
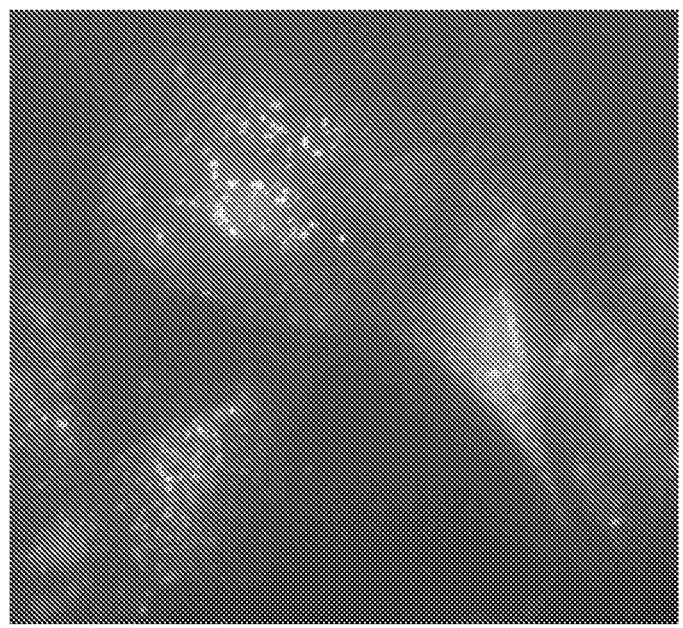

Dispersed rat pituitary cells were cultured for 5 days and incubated in the (B) presence and (A) absence of 1 μM of a TSI with a GHRH Targeting Moiety for 60 minutes. Cells were fixed and probed with rabbit antibody to light chain of the TSI and Goat anti-rabbit Alexa Fluor® 488. Nuclei were stained using Hoescht stain. A) nuclei shown in pale grey with no punctate white spots detected. (B) nuclei shown stained in pale grey. White punctuate spots indicates the presence of light chain of the TSI in endosomes (FIG. 4).

Example 9

Figure 5:
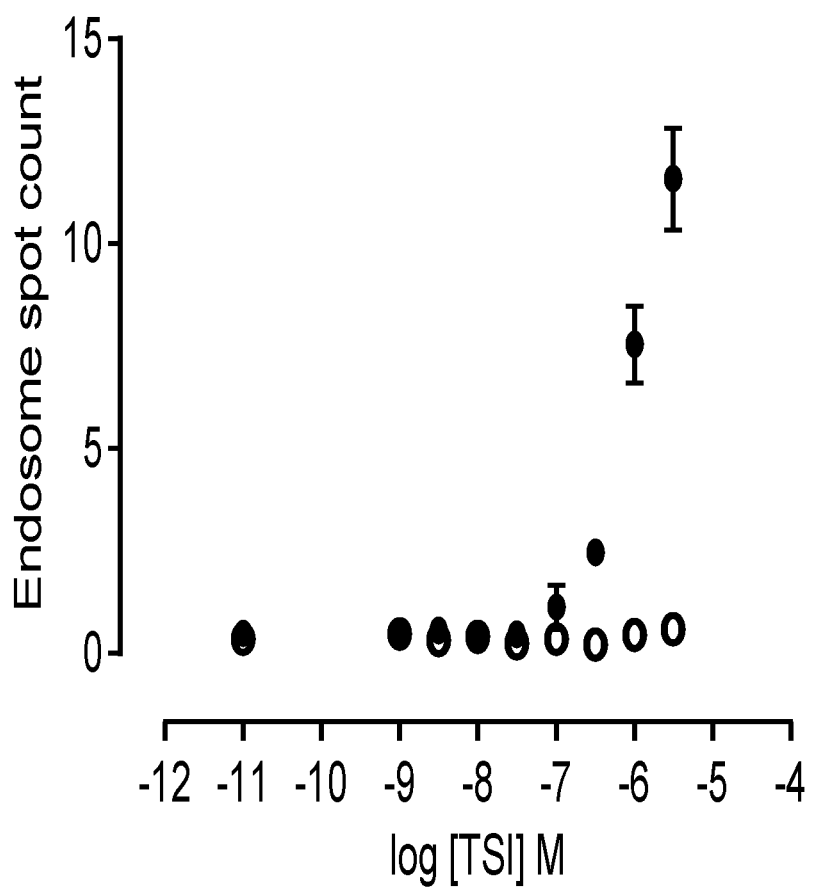

Dispersed rat pituitary cells were cultured for 5 days and were incubated in triplicate with increasing concentrations of a TSI having a GHRH targeting Moiety or the corresponding unliganded TSI for 60 minutes. Cells were fixed and probed with rabbit antibody to the light chain of the TSI and Goat anti-rabbit Alexa Fluor® 488. Endosome spot count was measured by high content screening. Data shown are mean±s.e. mean of triplicates obtained in one experiment (FIG. 5).

Example 10

Figure 6:
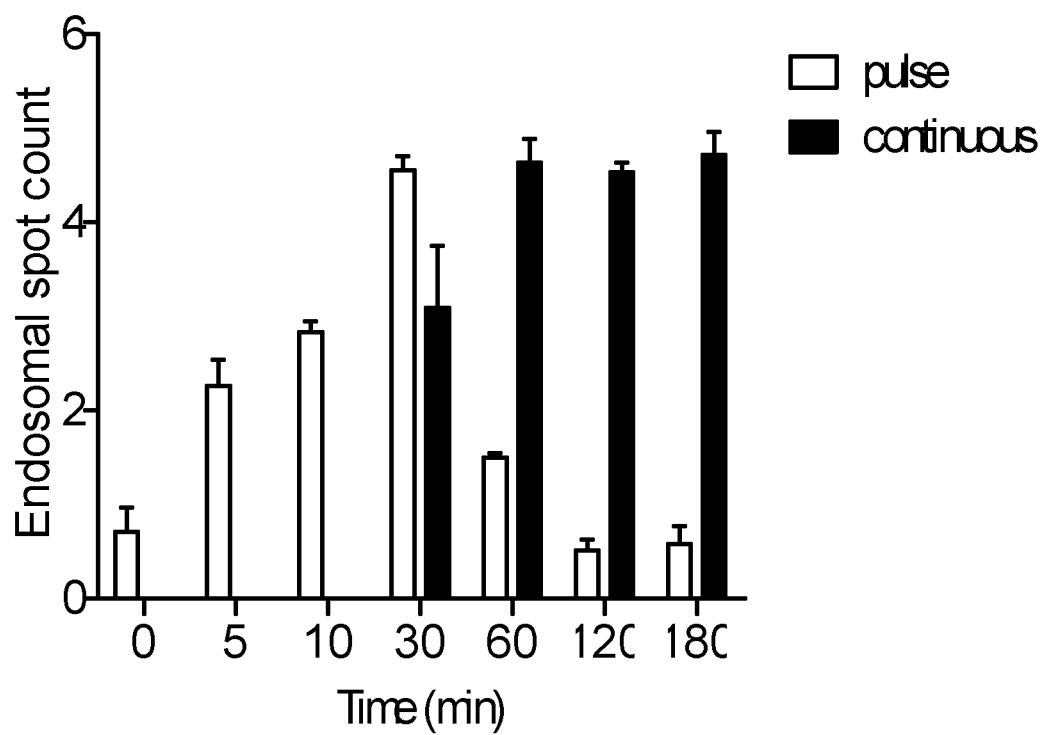

GH3 cells expressing the rat GHRH-R were seeded into 96-well plates and incubated overnight. Cells were incubated in triplicate with 1 μM of a TSI having a GHRH Targeting Moiety for increasing time periods after which cells were fixed and probed with rabbit antibody to light chain of the TSI and Goat anti-rabbit Alexa Fluor® 488. Cells were incubated continuously with TSI or were pulsed with TSI for 30 minutes and then washed before they were incubated for increasing time periods (30, 90, 150 min). At these time points cells were fixed and subsequently probed with antibody to the light chain of D. Endosome spot count was measured by high content screening. Data are the mean±s.e. mean of that obtained in three experiments performed in triplicate (FIG. 6).

Example 11

Figure 7:
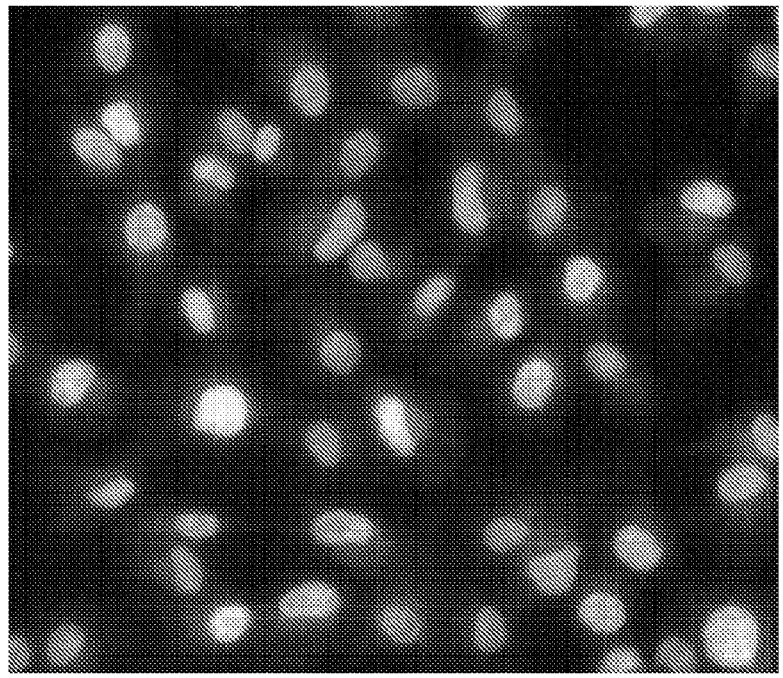
Figure 7:
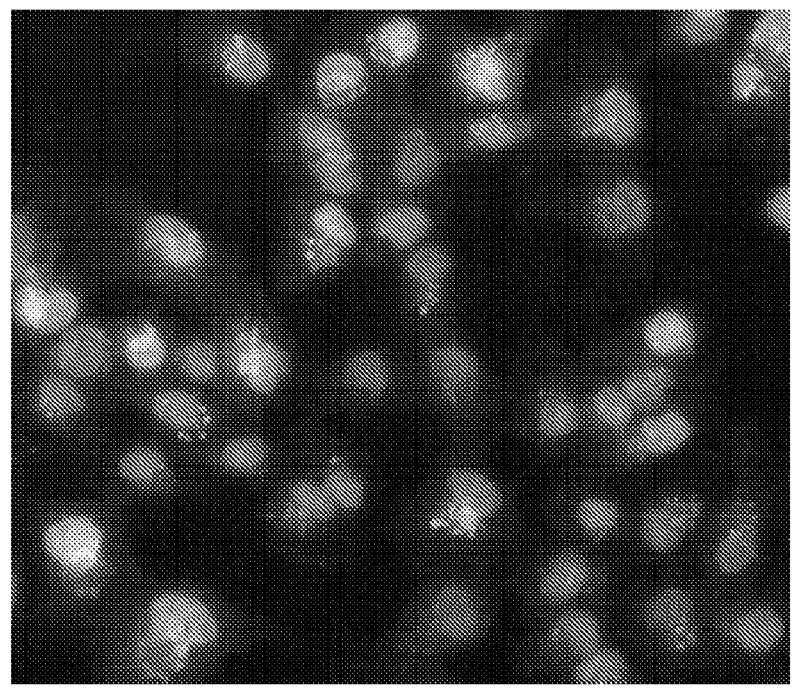

HT-1080 cells expressing the human EGFR were seeded in 96-well plates and incubated in the (B) presence and (A) absence of 2 μM of a TSI with a EGFR Targeting Moiety for 60 minutes. Cells were fixed and probed with rabbit antibody to light chain of the TSI and Goat anti-rabbit Alexa Fluor® 488. Nuclei were stained using Hoescht stain. (A) nuclei shown in pale grey with no punctate white spots detected. (B) nuclei shown stained in pale grey. White punctuate spots indicates the presence of light chain of the TSI in endosomes (FIG. 7).

Example 12

Figure 8:
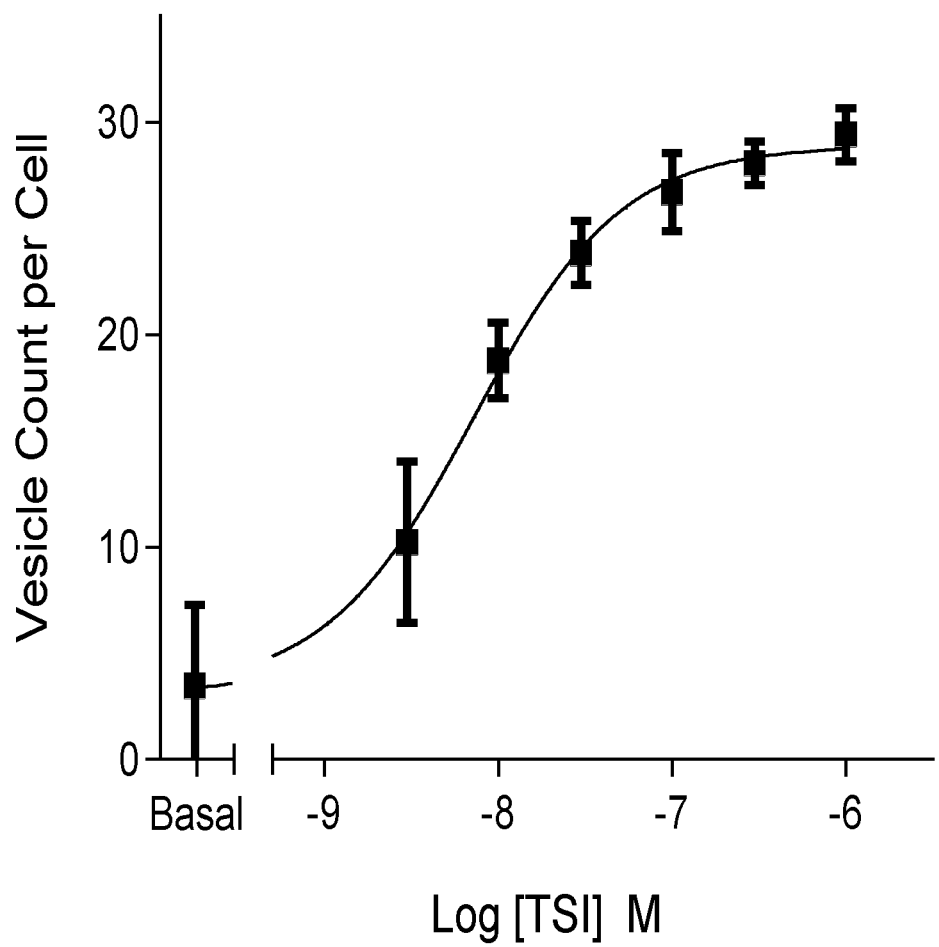

CHO-K1 cells expressing the GHRHR are seeded into 96-well plates and incubated overnight. Cells were incubated in triplicate with increasing concentrations of a TSI having a GHRH targeting moiety and translocation and light chain domains of serotype A botulinum neurotoxin for 30 min. Cells were fixed, permeabilised with digitonin and probed with rabbit antibody to the light chain of the TSI and Goat anti-rabbit Alexa Fluor® 488. Vesicle count per cell was measured by high content screening. Data shown are mean±s.e. mean of 3 experiments performed in triplicate (FIG. 8).

The invention claimed is:

1. An assay for assessing the endosome release ability of a test molecule,
   wherein said test molecule is a clostridial neurotoxin or a re-targeted non-cytotoxic protease (Targeted Secretion Inhibitor) in which the natural binding ability of the non-cytotoxic protease has been modified by the introduction of a binding ligand or Targeting Moiety, and
   wherein said test molecule has the ability to proteolytically cleave and inactivate a SNARE protein;
   said assay comprising:
   i) contacting a eukaryotic cell with a test molecule that is to be assessed for endosome release ability, wherein said eukaryotic cell comprises a cell membrane including a Binding Site present on the outer surface of the cell membrane of said cell;
   ii) incubating the test molecule with said eukaryotic cell, and thereby allowing
   a) the test molecule to bind to and form a bound complex with the Binding Site present on the eukaryotic cell, thereby permitting said bound complex to enter the eukaryotic cell by endocytosis;
   b) one or more endosomes to form within said cell, wherein the one or more endosomes contain the test molecule; and
   c) said test molecule to enter the cytosol of the eukaryotic cell by crossing the endosomal membrane of the one or more endosomes;
   iii) removing excess test molecule that is not bound to the Binding Sites present on the eukaryotic cells;
   iv) after a predetermined period of time, detecting the amount of test molecule present in the one or more endosomes, or detecting the amount of test molecule present in the cytosol of said eukaryotic cell;
   v) comparing the amount of test molecule detected in step iv) with a control value, wherein said control value represents the amount of test molecule present in the one or more endosomes or the amount of test molecule present in the cytosol prior to step iv);
   vi) calculating an endosome release value for the test molecule by determining the relative change in the amount of test molecule that is present within the one or more endosomes, or by determining the relative change in the amount of test molecule present in the cytosol of said eukaryotic cell;
   wherein step (iv) comprises detecting the test molecule using a fluorescent label.

2. The assay according to claim 1, wherein the eukaryotic cell is selected from the group consisting of a yeast cell, an insect cell, a vertebrate cell, a mammalian cell, a plant cell, and a fungal cell.

3. The assay according to claim 1, wherein incubation step ii) proceeds for a time period from 5 minutes to 5 days.

4. The assay according to claim 1, wherein detection step iv) is performed between 5 minutes and 5 hours following step iii).

5. An assay for assessing the inhibitory effects of a blocking molecule on endosomal transport in a eukaryotic cell, said assay comprising:
   i) contacting a eukaryotic cell with a control molecule that binds to a Binding Site present on the surface of said eukaryotic cell, wherein said control molecule is a clostridial neurotoxin or a re-targeted non-cytotoxic protease (Targeted Secretion Inhibitor) in which the natural binding ability of the non-cytotoxic protease has been modified by the introduction of a binding ligand or Targeting Moiety, and wherein said control molecule has the ability to proteolytically cleave and inactivate a SNARE protein, wherein said control molecule forms a bound complex with the Binding Site, enters the eukaryotic cell by endocytosis during which an endosome is formed that contains the control molecule, and wherein said control molecule enters the cytosol of the eukaryotic cell by crossing the endosomal membrane of the endosome;
   ii) incubating the control molecule with said eukaryotic cell, and thereby allowing
   a) the control molecule to bind to and form a bound complex with the Binding Site present on the eukaryotic cell, thereby permitting said bound complex to enter the eukaryotic cell by endocytosis;
   b) one or more endosomes to form within said cell, wherein the one or more endosomes contain the control molecule; and c) said control molecule to enter the cytosol of the eukaryotic cell by crossing the endosomal membrane of the one or more endosomes;
iii) contacting the eukaryotic cell with a test inhibitor molecule that is to be assessed for its ability to suppress endosomal release of control molecule from endosomes;
iv) after a predetermined period of time, detecting the amount of control molecule present in the one or more endosomes, or detecting the amount of control molecule present in the cytosol of said eukaryotic cell;
v) comparing the amount of control molecule detected in step iv) with a control value, wherein said control value represents the amount of control molecule present in the one or more endosomes or the amount of control molecule present in the cytosol prior to step iii);
vi) assigning an inhibition value for the test inhibitor molecule by determining the relative change in the amount of control molecule that is present within the one or more endosomes, or by determining the relative change in the amount of control molecule present in the cytosol of said eukaryotic cell wherein step (iv) comprises detecting the control molecule using a fluorescent label.

6. The assay according to claim 5, wherein the eukaryotic cell is selected from the group consisting of a yeast cell, an insect cell, a vertebrate cell, a mammalian cell, a plant cell, and a fungal cell.

7. The assay according to claim 5, wherein incubation step ii) proceeds for a time period from 5 minutes to 5 days.

8. The assay according to claim 5, wherein detection step iv) is performed between 5 minutes and 5 hours following step iii).

9. The assay according to claim 5, wherein contacting step iii) is performed between 5 minutes and 5 days following the start of incubation step ii).

10. The assay according to claim 3, wherein incubation step ii) proceeds for a time period from 1-12 hours, 2-10 hours, 4-8 hours or 6-8 hours.

11. The assay according to claim 4, wherein detection step iv) is performed between 15-240 minutes, 30-180 minutes or 45-150 minutes following step iii).

12. The assay according to claim 7, wherein incubation step ii) proceeds for a time period from 1-12 hours, 2-10 hours, 4-8 hours or 6-8 hours.

13. The assay according to claim 8, wherein detection step iv) is performed between 15-240 minutes, 30-180 minutes or 45-150 minutes following step iii).

14. The assay according to claim 9, wherein contacting step iii) is performed between 30 minutes and 12 hours, between 30 minutes and 10 hours, between 30 minutes and 8 hours or between 1-8 hours following the start of incubation step ii).

* * * * *